United States Patent [19]

Quadri

[11] Patent Number: 5,282,826
[45] Date of Patent: Feb. 1, 1994

[54] DISSECTOR FOR ENDOSCOPIC AND LAPAROSCOPIC USE

[75] Inventor: Arshad Quadri, Pittsfield, Mass.

[73] Assignee: Quadtello Corporation, Pittsfield, Mass.

[21] Appl. No.: 846,117

[22] Filed: Mar. 5, 1992

[51] Int. Cl.$^5$ ............................................ A61B 17/28
[52] U.S. Cl. .................................... 606/207; 81/90.2; 81/387
[58] Field of Search ............... 606/205, 206, 208, 210, 606/170, 198, 46, 51, 52, 207; 604/106; 81/90.2, 381, 383, 383.5, 385–387, 418, 420; 128/751

[56] References Cited

U.S. PATENT DOCUMENTS

| | | |
|---|---|---|
| 1,127,948 | 2/1915 | Wappler . |
| 1,150,214 | 8/1915 | London . |
| 2,109,147 | 2/1938 | Grosso ............................. 81/410 X |
| 2,507,710 | 5/1950 | Grosso ............................. 606/208 X |
| 4,763,669 | 8/1988 | Jaeger ............................. 606/170 X |
| 4,841,949 | 6/1989 | Shimizu et al. ......................... 128/4 |
| 4,887,612 | 12/1989 | Esser et al. ........................ 606/208 X |
| 4,919,112 | 4/1990 | Siegmund ............................ 128/4 |

FOREIGN PATENT DOCUMENTS 351165  1/1990  European Pat. Off. ............ 606/205
2737014 3/1979  Fed. Rep. of Germany .
980703  12/1982 U.S.S.R. .

Primary Examiner—Michael H. Thaler
Attorney, Agent, or Firm—Mason, Fenwick & Lawrence

[57] ABSTRACT

A surgical instrument comprising an elongated tubular hollow shaft, first and second opposable jaws pivotable at the distal end of the shaft, and first and second opposable dissecting tips pivotable at the ends of the jaws. The jaws are generally pivotable in first and second parallel planes and the tips are pivotable in third and fourth planes which are generally perpendicular to the first and second planes, respectively. A first handle is fixedly attached to the proximal end of the hollow shaft, and a second handle is pivotably connected to the first handle. The jaws are opened and closed by a rod which extends through the hollow shaft and has one end connected to the first and second jaws and its other end connected to the second handle. The angle of the tips is adjusted by a trigger plate pivotably attached to the first handle, and first and second wires attached at one end to the trigger plate and at the other end to the first and second tips, respectively. The first and second wires extend through a hollow guide tube having a longitudinal axis parallel to the shaft longitudinal axis and affixed to the shaft.

10 Claims, 2 Drawing Sheets

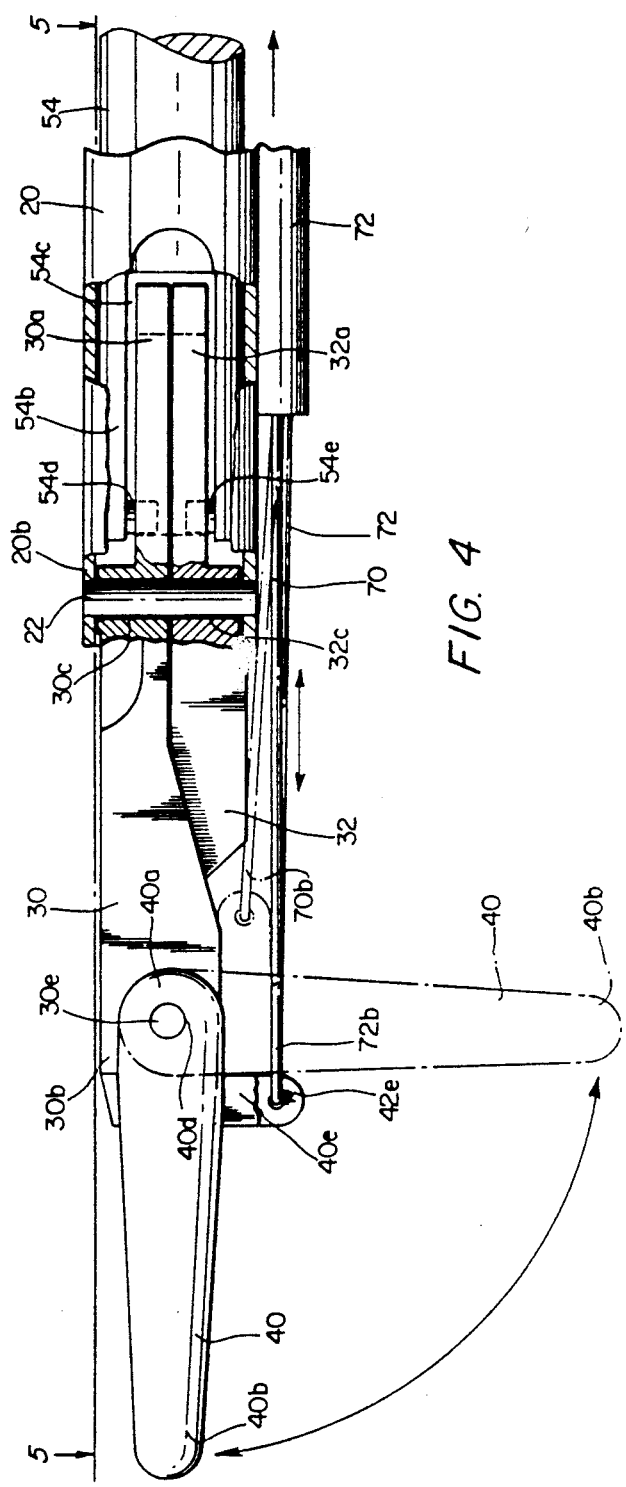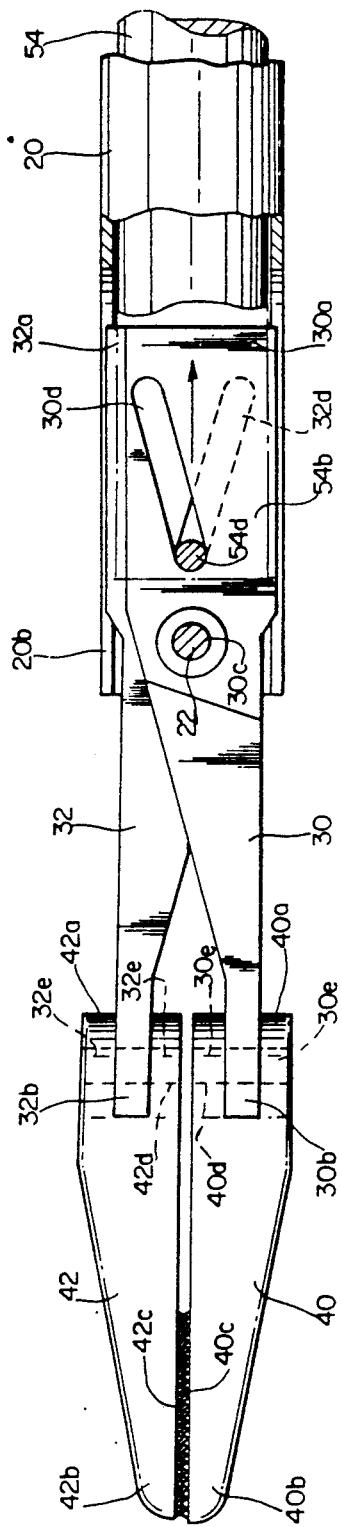

DISSECTOR FOR ENDOSCOPIC AND LAPAROSCOPIC USE

BACKGROUND OF THE INVENTION

1. Field of the Invention

The present invention relates to an instrument for use in laparoscopic and endothoracic surgery. More specifically, the invention relates to an endoscopic or laparoscopic dissector which has a variable-angle dissecting tip.

2. Related Art

Numerous designs are known for endoscopic dissectors for use in laparoscopic and endothoracic surgery. However, all of the dissectors which are presently commercially available have one feature in common, a fixed dissecting tip. More precisely, the tips which carry the dissecting blades ar fixed in position except to the extent that they ar capable of reciprocatible movement to effect cutting or dissection. In general, the tips in their enclosed (non-cutting or non-dissecting) position are aligned with the main tube of the dissector lure are slightly bent with respect thereto.

Examples of commercially-available dissectors having fixed tips are the dolphin nose, Maryland, and right angle dissectors. Additional dissectors having fixed tips are shown in U.S. Pat. No. 1,127,948 to Wappler; U.S. Pat. No. 1,150,214 to London; and West German Patent No. 27 37 014 to Wolf.

USSR Patent No. 980,703 discloses a tissue cutting instrument having two cutters 4 and 5 which are activated by rack and pinion drives from finger levers, both for cutting and for rotation 360 degrees about their pivot axis. However, this type of instrument is suitable only for those applications in which cutting is to be achieved by a true scissor action, because rotation for both cutting and pivoting purposes occurs about a single pivot axis. It is not suitable for pivoting of opposable cutting blades such as those disclosed by Wappler.

SUMMARY OF THE INVENTION

It is therefore a primary object of the present invention to provide a dissector for laparoscopic or endoscopic use in which the dissecting tips are both opposable for dissecting and rotatable for changing the angle of the tips with respect to the body of the instrument.

This and other objects of the invention are achieved by a surgical instrument comprising an elongated tubular hollow shaft, first and second opposable jaws pivotable at one end of the shaft, and first and second opposable dissecting tips pivotable at the ends of the jaws.

The jaws are pivotable about a first pivot axis perpendicular to the shaft longitudinal axis between an open position and a closed position, the first pivot axis extending through the distal end of the hollow shaft. The first and second opposable jaws have respective first and second longitudinal axes each intersecting the first pivot axis at a right angle and respectively defining with the first pivot axis first and second planes.

The first dissecting tip is pivotably connected to the outer end of the first jaw about a second pivot axis perpendicular to the first plane, while the second dissecting tip is pivotably connected to the outer end of the second jaw about a third pivot axis perpendicular to the second plane. In simplified terms, the jaws are generally pivotable in first and second parallel planes and the tips are pivotable in third and fourth planes which are generally perpendicular to the first and second planes. A first handle is fixedly attached to the proximal end of the hollow shaft, and a second handle is pivotably connected to the first handle.

The jaws are opened and closed by a rod which extends through the hollow shaft and has its first end connected to the first and second jaws and its second end connected to the second handle. The angle of the tips is adjusted by a trigger plate pivotably attached to the first handle, and first and second wires attached at one end to the trigger plate and at the other end to the first and second tips, respectively. The first and second wires extend through a hollow guide tube having a longitudinal axis parallel to the shaft longitudinal axis and affixed to the shaft.

A locking mechanism ca be provided to lock the trigger plate in position.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIG. 4 is an enlarged side elevational view, partially in cross-section, of the jaws and cutting tips of the universal dissector of FIG. 1.

FIG. 5 is an enlarged top plan view, partially in cross-section, of the jaws and cutting tips of the universal dissector of FIG. 1.

DETAILED DESCRIPTION OF THE PREFERRED EMBODIMENTS

Figure 1:
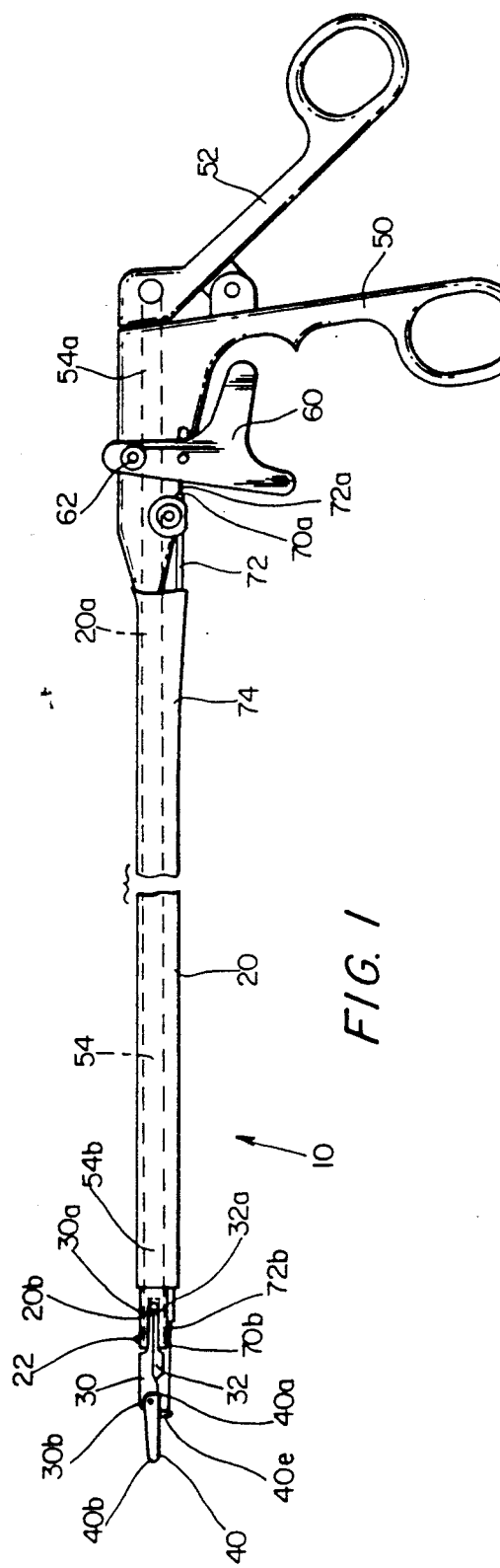
FIG. 1 is a side elevational view of a universal dissector in accordance with the present invention.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

Figure 2:
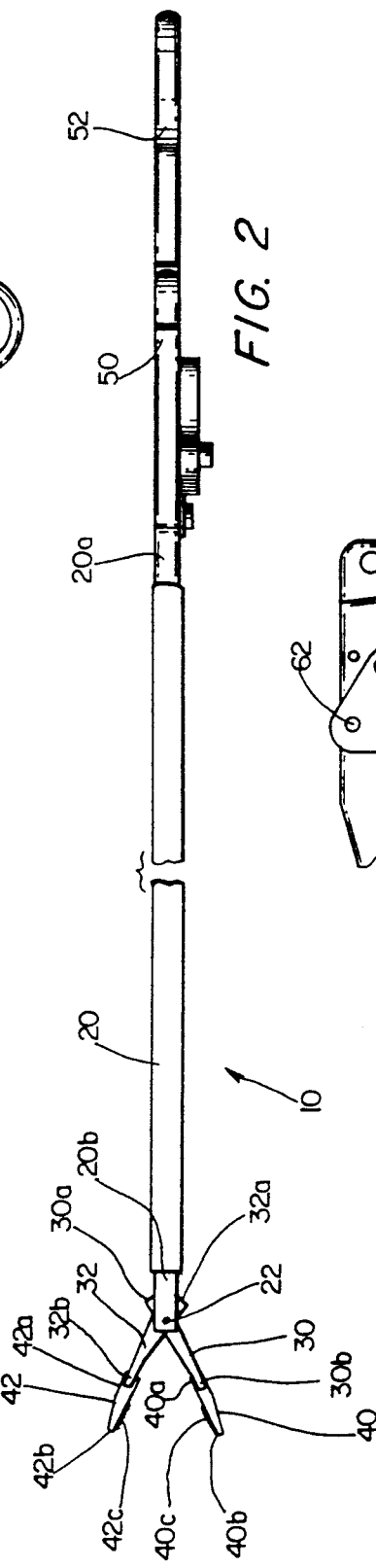
FIG. 2 is a top plan view of the universal dissector of FIG. 1.

Referring now to FIGS. 1 and 2, there is shown a universal dissector 10 in accordance with the present invention. Dissector 10 includes an elongated tubular hollow shaft 20 having a proximal end 20a and a distal end 20b. A pivot pin 22 extends through distal end 20b perpendicular to the longitudinal axis of shaft 20, and defines a first pivot axis.

As can best be seen in FIGS. 4 and 5, first and second opposable jaws 30 and 32 having respective proximal ends 30a and 32a and respective distal ends 30b and 32b are pivotable about pivot pin 20. Jaws 30 and 32 have longitudinal axes which are generally coplanar with the shaft longitudinal axis, which intersect the first pivot axis, and which respectively define first and second planes with the first pivot axis.

Jaws 30 and 32 further include respective cylindrical apertures 30c and 32c, angled slots 30d and 32d, and integral pivot pins 30e and 32e. Intermediate cylindrical approximately intermediate their proximal and distal ends, for receiving pivot pin 20, and thus are coplanar with the first and second planes. Angled slots 30d and 32d are positioned respectively between cylindrical aperture 30c and proximal end 30a of jaw 30 and between cylindrical aperture 32c and proximal end 32a of jaw 32, for a purpose to be described hereinafter. Integral pivot pins 30e and 32e are positioned at distal ends 30b and 32b, respectively, and extend outwardly from jaws 30 and 32 perpendicular to the first and second planes, also for a purpose to be described hereinafter. Pivot pins 30e and 32e respectively define second and third pivot axes which are respectively perpendicular to the first and second planes.

A first dissecting tip 40 is pivotably connected to distal end 30b of jaw 30, and a second dissecting tip 42 is pivotably connected to distal end 32b of jaw 32. Tips 40 and 42 have respective proximal ends 40a and 42a and respective distal ends 40b and 42b, and are provided with opposable serrated faces 40c and 42c. Other than the serrations on faces 40c and 42c, all parts of tips 40 and 42 are smooth to avoid incurring damage to delicate structures.

Proximal ends 40a and 42a are forked, and have respective discontinuous cylindrical apertures 40d and 42d therethrough for receiving pivot pins 30e and 32e, respectively. Thus, dissecting tip 40 pivots about the second pivot axis perpendicular to the first plane, while dissecting tip 42 pivots about the third pivot axis perpendicular to the second plane.

Tips 40 and 42 are provided at their lower edges with downwardly-extending ears 40e and 42e generally perpendicular to the longitudinal axes of tips 40 and 42, for a purpose to be described hereinafter.

A first handle 50 is fixedly attached to proximal end 20a of shaft 20, while a second handle 52 is pivotably connect to first handle 52, for operating jaws 30 and 32, in a manner to be described hereinafter. A rod 54 extends through shaft 20 and has its proximal end 54a pivotably connected to second handle 52 and its distal end 54b slidably connected to first and second jaws 30 and 32.

In particular, as shown in FIG. 4, distal end 54b is forked to define a slot 54c which is provided with inwardly extending, upper and lower pins 54d and 54e. Upper and lower pins 54d and 54e slidingly engage slots 30d and 32d, respectively, in jaws 30 and 32. Thus, when handle 52 is rotated towards handle 50, rod 54 is moved axially towards the user and upper and lower pins 54d and 54e slide respectively in slots 30d and 32d to cause jaws 30 and 32 to open. Conversely, when handle 52 is rotated away from handle 52, rod 54 is moved axially away from the use and upper and lower pins 54d and 54e slide respectively in slots 30d and 32d to cause jaws 30 and 32 to close.

The angle of tips 40 and 42 relative to jaws 30 and 32 is regulated by a control mechanism including a control trigger or plate 60 pivotable about a pin or screw 62 affixed to first handle 50, and first and second wires 70 and 72. First and second wires have proximal ends 70a and 72a which are fixedly attached to plate 60 at a point offset from pin 62, and distal ends 70b and 72b which are fixedly attached to ears 40e and 42e, respectively, of tips 40 and 42. Thus, when plate 60 is rotated about pin 62, wires 70 and 72 are moved longitudinally, causing tips 40 and 42 to rotate about their pivot axes.

Preferably, wires 70 and 72 extend through a hollow guide tube 72 having a longitudinal axis parallel to the shaft longitudinal axis and affixed to shaft 20 on the same side as plate 60. Shaft 20 and guide tube 72 can be surrounded along substantially their entire length by an insulating rubber sheath 74 for insulating shaft 20 during diathermy.

Figure 3:
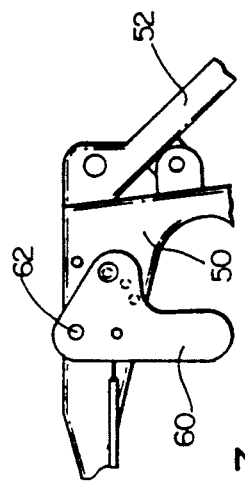
FIG. 3 is a side elevational view of an alternative embodiment of the cutting tip control mechanism of the universal dissector of FIG. 1.

Plate 60 can be maintained in its desired position either by friction, as shown in FIGS. 1 and 2; or by a locking mechanism, for example a detent ball and a series of dimples in the facing surfaces of plate 60 and first handle 50, as shown in FIG. 3.

In use, dissector 10 is through a trocar in conventional fashion to reach to surgical site, with tips 40 and 42 extended straight out, i.e., with their longitudinal axes collinear with the longitudinal axes of jaws 30 and 32. Once tips 40 and 42 are through the trocar and are positioned at the surgical site, they can be rotated up to 90° to the desired angle. In the event of any malfunction in the mechanism which adjusts the angle of tips 40 and 42, tips 40 and 42 can be straightened prior to removal by simple pressure against the trocar.

Modifications and variations of the above-described embodiments of the present invention are possible, as appreciated by those skilled in the art in light of the above teachings. For example, mechanisms other than that disclosed herein can be employed to open and close the jaws.

It is therefore to be understood that, within the scope of the appended claims and their equivalents, the invention may be practiced otherwise than as specifically described.

What is claimed is:

1. A surgical instrument comprising:
   an elongated tubular hollow shaft having a proximal end, a distal end, and a shaft longitudinal axis;
   first and second opposable jaws each having an proximal end and an distal end and being pivotable about a first pivot axis perpendicular to said shaft longitudinal axis between an open position and a closed position, said first pivot axis extending through said distal end of said hollow shaft, said first and second opposable jaws having respective first and second longitudinal axes each intersecting said first pivot axis at a right angle and respectively defining with said first pivot axis first and second planes;
   a first dissecting tip pivotably connected to said distal end of said first jaw about a second pivot axis perpendicular to said first plane;
   a second dissecting tip pivotably connected to said distal end of said second jaw about a third pivot axis perpendicular to said second plane;
   activating means for moving said first and second jaws between said open and closed positions; and
   adjustment means for pivoting said first and second dissecting tips about said second and third pivot axes, respectively.

2. The surgical instrument of claim 1, wherein said activating means comprises:
   a first handle fixedly attached to said proximal end of said hollow shaft;
   a second handle pivotably connected to said first handle; and
   a rod extending through said hollow shaft and having a first end connected to said first and second jaws and a second end connected to said second handle.

3. The surgical instrument of claim 2, wherein said adjustment means comprises:
   a first wire having a first end connected to said first dissecting tip and a second end opposite said first end;

a second wire having a first end connected to said second dissecting tip and a second end opposite said first end; and a plate pivotably mounted on said first handle, said plate being connected to said second ends of said first and second wires and including locking means for locking said plate in a desired position.

4. The surgical instrument of claim 3, wherein said locking means locks said plate with respect to said first handle.

5. The surgical instrument of claim 1, wherein said adjustment means comprises:

a first wire having a first end connected to said first dissecting tip and a second end opposite said first end;

a second wire having a first end connected to said second dissecting tip and a second end opposite said first end; and control means for longitudinally moving said first and second dissecting tip wires, said adjustment means being positioned proximate said proximal end of said shaft and being connected to said second ends of said first and second dissecting tip wires.

6. The surgical instrument of claim 5, further comprising a hollow guide tube having a longitudinal axis parallel to said shaft longitudinal axis, wherein said first and second wires extend through said hollow guide tube.

7. A surgical instrument comprising:

an elongated tubular hollow shaft having a proximal end, a distal end, and a shaft longitudinal axis;

first and second opposable jaws each having a proximal end and a distal end and being pivotable about a first pivot axis perpendicular to said shaft longitudinal axis between an open position and a closed position, said first pivot axis extending through said distal end of said hollow shaft, said first and second opposable jaws having respective first and second longitudinal axes each intersecting said first pivot axis at a right angle and respectively defining with said first pivot axis first and second planes;

a first dissecting tip pivotably connected to said distal end of said first jaw about a second pivot axis perpendicular to said first plane;

a second dissecting tip pivotably connected to said distal end of said second jaw about a third pivot axis perpendicular to said second plane;

a first handle fixedly attached to said proximal end of said hollow shaft;

a second handle pivotably connected to said first handle a rod extending through said hollow shaft and having a first end connected to said first and second jaws and a second end connected to said second handle;

a first wire having a first end connected to said first dissecting tip and a second end opposite said first end;

a second wire having a first end connected to said second dissecting tip and a second end opposite said first end; and adjustment means for longitudinally moving said first and second wires, said adjustment means being connected to said second ends of said first and second wires.

8. The surgical instrument of claim 7, further comprising a hollow guide tube having a longitudinal axis parallel to said shaft longitudinal axis, wherein said first and second wires extend through said hollow guide tube.

9. The surgical instrument of claim 7, further comprising locking means for locking said adjustment means in position.

10. A surgical instrument comprising:

an elongated tubular hollow shaft having a proximal end, a distal end, and a shaft longitudinal axis;

first and second opposable jaws each having a proximal end and a distal end and being pivotable in first and second parallel planes, respectively, about a first pivot axis perpendicular to said shaft longitudinal axis between an open position and a closed position, said first pivot axis extending through said distal end of said hollow shaft;

a first dissecting tip pivotably connected to said outer end of said first jaw for rotation in a third plane perpendicular to said first plane;

a second dissecting tip pivotably connected to said outer end of said second jaw for rotation in a fourth plane perpendicular to said second plane;

activating means for moving said first and second jaws between said open and closed positions; and adjustment means for pivoting said first and second dissecting tips in said third and fourth planes, respectively.

* * * * *